(12) United States Patent
Xue

(10) Patent No.: US 7,769,434 B2
(45) Date of Patent: Aug. 3, 2010

(54) METHOD OF PHYSIOLOGICAL DATA ANALYSIS AND MEASUREMENT QUALITY CHECK USING PRINCIPAL COMPONENT ANALYSIS

(75) Inventor: Joel Qiuzhen Xue, Germantown, WI (US)

(73) Assignee: General Electric Company, Schenectady, NY (US)

(*) Notice: Subject to any disclaimer, the term of this patent is extended or adjusted under 35 U.S.C. 154(b) by 684 days.

(21) Appl. No.: 11/564,870

(22) Filed: Nov. 30, 2006

(65) Prior Publication Data

US 2008/0132799 A1 Jun. 5, 2008

(51) Int. Cl.
*A61B 5/0402* (2006.01)
(52) U.S. Cl. ...................... 600/509; 600/515
(58) Field of Classification Search .............. 600/509, 600/513, 516, 517, 515
See application file for complete search history.

(56) References Cited

U.S. PATENT DOCUMENTS

| | | | | |
|---|---|---|---|---|
| 5,560,368 | A * | 10/1996 | Berger | 600/517 |
| 5,967,995 | A * | 10/1999 | Shusterman et al. | 600/516 |
| 7,702,502 | B2 * | 4/2010 | Ricci et al. | 704/205 |
| 2003/0004652 | A1 * | 1/2003 | Brunner et al. | 702/19 |
| 2005/0234363 | A1 * | 10/2005 | Xue | 600/515 |
| 2007/0167846 | A1 * | 7/2007 | Sternickel et al. | 600/509 |
| 2007/0208263 | A1 * | 9/2007 | John et al. | 600/509 |

OTHER PUBLICATIONS

Karjalainen, P.A.; Tarvainen, M.R.; Laitinen, T., "Principal Component Regression Approach for QT Variability Estimation," Engineering in Medicine and Biology Society, 2005. IEEE-EMBS 2005. 27th Annual International Conference , vol., no., pp. 1145-1147, Jan. 17-18, 2006.*
Moody, G.B.; Mark, R.G., "QRS morphology representation and noise estimation using the Karhunen-Loeve transform," Computers in Cardiology 1989, Proceedings. , vol., no., pp. 269-272, Sep. 19-22, 1989.*
"QT Analysis Tool," Marquette Electronics Inc, algorithm manual, Available to applicant Oct. 13, 2004.*
Appendix A—ECG Interval Editor Option—30 pages, 2006.
QT Analysis Tool—pp. 1-2, Oct. 13, 2004.

* cited by examiner

*Primary Examiner*—Carl H Layno
*Assistant Examiner*—Pamela M Bays
(74) *Attorney, Agent, or Firm*—Andrus, Sceales, Starke & Sawall, LLP

(57) ABSTRACT

In a method of analyzing patient physiological data, the data is subjected to principal component analysis and compared to a model physiological data principal component analysis. The comparison is used to identify correlations present in the morphology of the patient physiological data. The present invention further includes determining a confidence interval for the detection of a morphological feature and utilizing this confidence interval for improving the quality of the detection of morphological features of the patient physiological data, including automated morphological feature identification.

20 Claims, 7 Drawing Sheets

METHOD OF PHYSIOLOGICAL DATA ANALYSIS AND MEASUREMENT QUALITY CHECK USING PRINCIPAL COMPONENT ANALYSIS

FIELD OF THE INVENTION

The present invention relates to the analysis of physiological data, for example cardiographic data. More specifically, the present invention relates to a technique for identifying features of the data that are predictive of events, typically future events, in the physiological function of a patient. Such identification of features in a collection of data is often termed "data mining". The technique of the present invention may also be used to improve quality control in automated physiological data analysis and may be used in pharmaceutical testing to be reported to a regulatory agency.

BACKGROUND OF THE INVENTION

Before a new drug may be marketed to the public, the Food and Drug Administration (FDA) requires that the drug be proven safe and efficacious for its intended purpose. This required proof necessitates that extensive testing and trials of a new drug be made and the results reported to the FDA before the drug may gain regulatory approval to be marketed.

Many drugs have intended or unintended effects on the heart or cardiac function of a patient. Thus, one aspect of the proof required for regulatory approval is extensive analysis of the effect of the drug on the patient's heart, which effect is often evidenced by the morphology or shape of an electrocardiogram (ECG) obtained from the patient. A detailed analysis of the patient's ECG morphology must look to a variety of ECG signal characteristics, including those features associated with the repolarization of the heart after contraction. Features associated with heart repolarization include T-wave duration, S-T morphology, U wave, Q-T interval and heart-rate corrected Q-T interval (QTc). Anomalies in these features are, in turn, often associated with life threatening cardiac tachycardia or arrhythmias so that a main purpose for the analysis of ECG morphology data is to determine whether there is a correlation between the tested drug and life threatening tachycardia or arrhythmias.

More specifically, evidence of drug induced Torsade-de-Pointes (TdP), or torsade, is sought by analyzing the patient's ECG morphology. TdP is a type of ventricular tachycardia, or arrhythmia, characterized by fluctuation of the QRS complexes around the ECG baseline. Currently, the only indication of TdP that is accepted by regulatory authorities are features relating to an elongated Q-T interval in the ECG morphology. Regulatory authorities are thus particularly interested in any correlation between the administration of a drug and a prolongation of a patient's Q-T interval.

With the regulatory authorities currently accepting Q-T interval as the primary or only feature to predict possible drug induced TdP, two challenges are presented to pharmaceutical testing. The first challenge is to improve Q-T interval related measurements to more accurately measure the Q-T interval and the corrected Q-T Interval (QTc). The measurement of Q-T interval and the calculation of QTc are complicated by the hysteresis effect of heart rate within a heart cycle. Because of the hysteresis effect, a change in heart rate and interval between identifying features in the heartbeat waveform (the R-R interval) may not be immediately followed by a change in Q-T interval. In the field of pharmaceutical testing, it is thus desired to provide more sophisticated methods for determining when Q-T interval should be collected rather than initiating the collection responsive to the detection of an R-R interval change.

Second, it is desirable, in practice, to have the ability to collect and analyze patient data to find new morphological features which may yield a better prediction of drug induced TdP than the currently accepted Q-T interval data. However the magnitude and complexity of data that must be analyzed to identify correlative features makes this a daunting task.

Therefore, it is desirable in the field of physiological data analysis, including that involving pharmaceutical testing, to develop a method for processing raw ECG data collected from drug trial subjects and for analyzing many ECG morphological features to identify complex correlations that are indicative of TdP or other drug induced adverse effects, such as arrhythmia.

SUMMARY OF THE INVENTION

The present invention provides a method for providing, in a pharmaceutical drug trial and other applications, an accurate measurement of the Q-T interval as well as the ability to find new ECG morphological features that might serve as a better indication of drug induced TdP.

In an embodiment, new T wave morphological features are used to analyze an ECG waveform. The new morphological features can be based on an individual lead, a composite beat formed from all leads or the eigenvectors obtained by principal component analysis (PCA).

In an embodiment, a score based on the new morphological features is generated, the score having a composite number categorizing the overall T wave morphology.

In an embodiment, a database of ECG signals is compiled for use as a reference library. This database is used to generate a model ECG principal component analysis that is compared against the principal component analysis of the collected ECG signal. The principal component analysis can facilitate the identification of correlations within the data. Alternatively the PCA can be used in automated morphological feature detection by determining confidence intervals for the detection of specific morphological features. The confidence intervals denote the certainty with which morphological features are identified.

In a further feature of the present invention, the collected ECG information is sent to an ECG reference library database, thereby updating the database and allowing the database to "learn" as the analysis of additional collected ECG signals proceeds.

BRIEF DESCRIPTION OF THE DRAWINGS

The invention will be further understood from the following detailed description, taken in conjunction with the drawings. In the drawings.

DETAILED DESCRIPTION

While the present invention is described using a determination of Q-T interval and a group of morphological features for exemplary purposes, it is understood that the method of the present invention is not so limited, but rather may be used for the determination of new morphological features of any relevant physiological signal, such as electromyography (EMG) and electroencepholography (EEG). A physiological signal comprising an electrocardiogram (ECG) is used in the description of the present invention as an example.

Figure 1A:
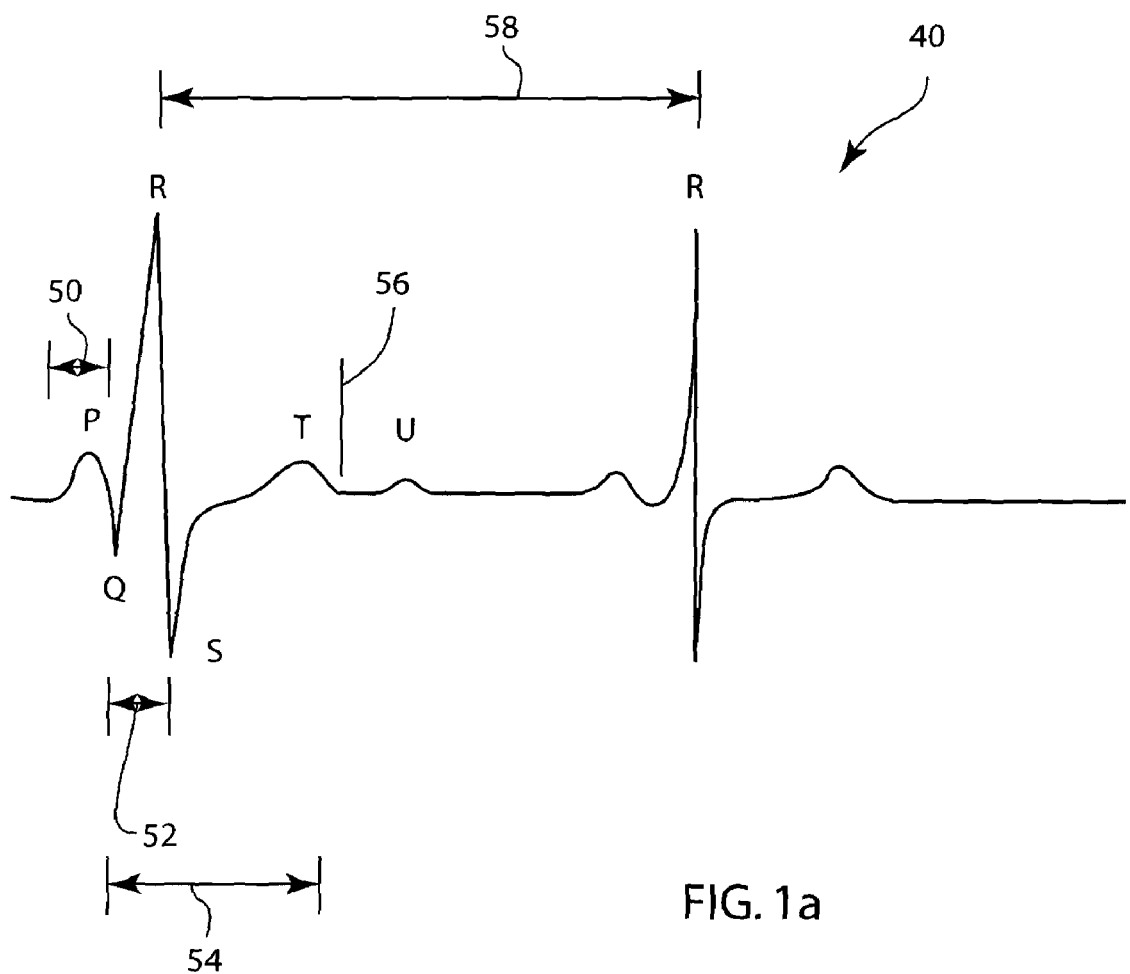
FIG. 1*a* depicts an ECG signal with the standard morphological features labeled.

FIG. 1a depicts a generalized ECG signal 40 with indications of some of the widely recognized morphological features that may be used in the data mining or automatic morphological detection aspects of the present invention. Many of the morphological features of an ECG signal 40 are related to the cyclical depolarization and repolarization of specific regions of the heart that characterize the contraction and relaxation phases of a cyclical heartbeat. The P-wave and the QRS complex are indicative of the depolarization of the heart atria and ventricles respectively. Therefore, the P duration 50 and the QRS duration 52 are indicative of the length of time that it takes for these regions of the heart to depolarize, thus initiating the contraction of the heart. The physical contraction of the heart muscle lasts for a time period beyond that of the time that it takes for the regions to depolarize. Other morphological features present in the ECG signal 40 are indicative of the repolarization of areas of the heart. The T-wave is one such morphological feature as the T-wave is indicative of the repolarization of the ventricle muscle. The much smaller U-wave is a morphological feature of the ECG signal that is indicative of the repolarization of the heart's natural pacemaker, the sinoatrial node.

Figure 1B:
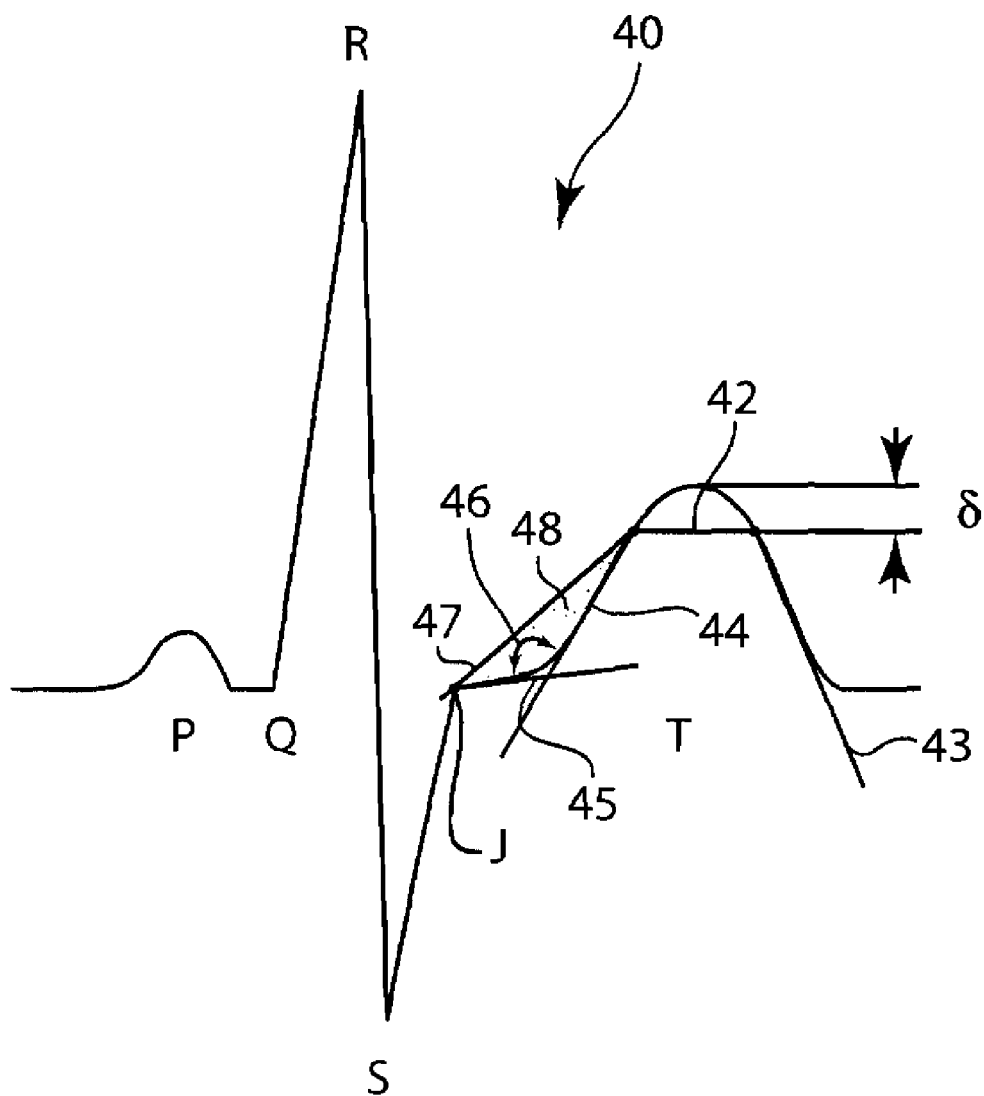
FIG. 1*b* depicts an ECG with the new T wave morphological features labeled.

FIG. 1b depicts a generalized ECG signal 40 and a plurality of new T wave morphological features. The new morphological features are more sensitive to changes in the ion channels of the cardiac cells caused by either congenital factors or by drug induced factors. The ECG signal 40 can be from an individual lead, a composite lead formed from all of the leads, such as the vector magnitude of a 12 lead ECG, or the ECG signal 40 can be from the eigenvectors obtained by principal component analysis. T peak line 42 is defined as a line segment that deviates in amplitude from the T wave maximum value within a predefined range, Delta (δ). The width of the T peak line 42 is denoted Tpw. The downward slope Kd of downslope line 43 is that of the least-square fitting line for the segment of the ECG signal 40 starting at the right end of the T peak line 42 and extending forward about 40 msec to the right as shown in FIG. 1b. The first upslope line 44, having a slope denoted as the value Ku1, is the least-square fitting line for segment of the ECG signal 40 the left end of T peak line 42 and extending to the left 50 msec. The second upslope line 45, denoted as the value Ku2, is the least-square fitting line for the segment of the ECG signal 40 starting at the left end of the first upslope line 44 and extending to the left about 50 msec. Angle 46, having a slope denoted as the value α, is the angle between the first upslope line 44 and the second upslope line 45. The angle 46 describes the nature of the T wave shape as either "concave down" or "concave up." Line 47 extends between the QRS offset (J point) to the left end of the Tpeak line 42. The T slope area 48, denoted as the value Tda, is the area bounded by the line 47 and the first 44 and second 45 upslope lines.

The distributions for each of the morphological parameters depicted in FIG. 1b are determined by data mining on several normal and abnormal ECG databases. In addition, the T wave may be scored based on the parameters representing the above mentioned morphological features. These parameters may include: the T peak line 42 width (Tpw), the slopes of the first upslope line 44 (Ku1), the second upslope line 45 (Ku2), and the down slope line 43 (Kd), the angle (a) of angle 46; and the absolute difference (Tsym) between the slope of the first upslope line 44 (Ku1) and the downslope line 43 (Kd). The score for a T wave may be written as:

$$TM\_score = a1*Tpw + a2*Kd + a3*Ku1 + a4*Ku1 + a4*\alpha + a6*Tda + a7*Tsym \quad (1)$$

where $a_1 \_ a_i$ are the model parameters.

Model parameters may be derived by a regression model commonly used in statistical analysis. The T wave score TM_score is distributed from 0 to 1, with 0 representing most normal T wave morphology, and the 1 representing most abnormal T wave morphology. An abnormal T wave morphology may be caused by congenital long QT, drug induced long QT, ischemia, or from TdP; however there are many other causes of abnormal T wave morphology contemplated within the scope of the present disclosure. During a modeling training stage, normal and abnormal T wave waveforms and an assigned TM score are presented. The results from the regression analysis include the score model coefficients and corresponding significance values.

Analysis among depolarization and repolarization features can be used to determine certain aspects of cardiological health. The Q-T interval 54, which is indicative of the length of time that the ventricles of the heart are contracted after the heart muscle has depolarized, is commonly used to identify potential tachycardia, or more specifically, TdP. The T-wave offset 56, or the end of the T-wave, shown in FIG. 1a, is another important morphological feature as it indicates when the ventricles have ended their repolarization, thus also indicating the end of the elevated blood pressure that characterizes the blood pressure systole. A further example of an ECG morphological feature that may be analyzed in an embodiment of the present invention is the R-R interval 58 shown in FIG. 1a, which marks the length of time between QRS complexes of the ECG signal of successions heart beats. The determination of the R-R interval can be used to determine the patient's heart rate.

Principal component analysis (PCA), as mentioned above is a statistical method used to simplify the information load when analyzing multivariate data. PCA is often used for feature selection in data mining applications. "Data mining" is a form of data processing or analysis using data searching capabilities and statistical algorithms, such as clustering, correlation, and neural networks, to discover patterns and correlations in large sets of data. The idea behind principal component analysis is that in any set of multivariate data, there will be correlated sets of data points. The more correlated two sets of data are, the more redundant it is to maintain both data points. For example, if variable data points x and y are perfectly correlated to each other it is not necessary to include representative data for both variables x and y since by knowing a particular value for one variable the value of the other variable will also be known. Therefore, if two variables within a set of multivariate data are correlated, we can conceptually eliminate one of the variables and not lose any data.

Figure 2A:
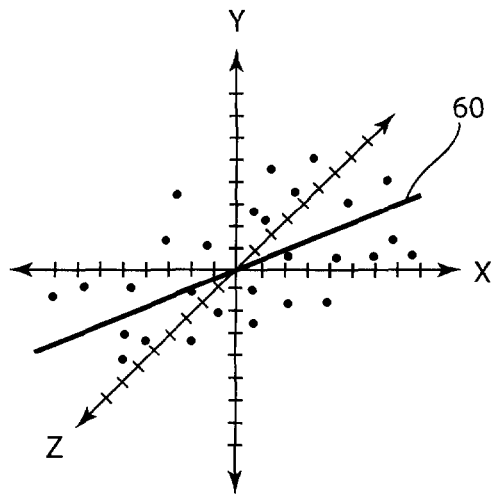
FIGS. 2*a*, 2*b*, and 2*c* depict a series of graphs visually representing the technique of principal component analysis.

FIG. 2 is used for an explanation of the basics of PCA. Depicted in FIG. 2a is a graph depicting some multivariate data points in three axes: x, y, and z. A linear regression line 60 indicates the correlation between the x coordinates and the z coordinates for each data point. For the purposes of example, it will be assumed that there is a high degree of correlation between linear regression line 60 and the x and z coordinates of the data.

Figure 2B:
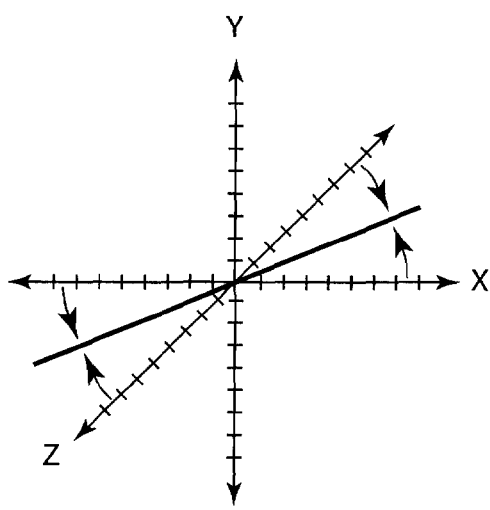

Now referring to FIG. 2b, assuming the high degree of correlation between the data points and the linear regression line 60, the x and the z coordinates of the data points are not both needed as they are closely correlated. By removing a principal component of the data, the data can be simplified. This is accomplished, in effect, by rotating the x axis and the z axis into the linear regression line 60. The linear regression line 60 now becomes the new simplified reference axis for the data points.

Figure 2C:
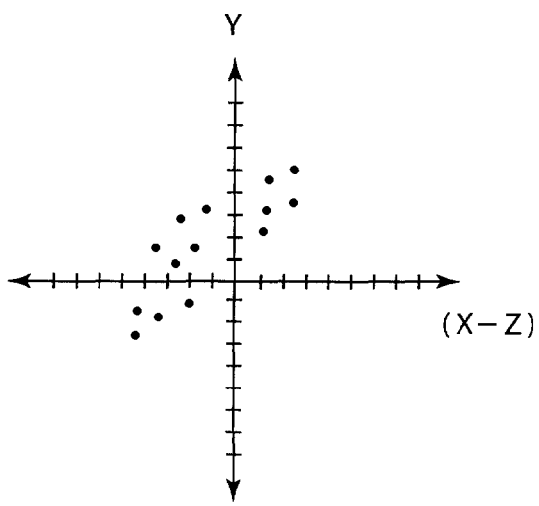

FIG. 2c depicts the new graphical representation of the data with respect to the y axis and the new (x-z) axis. Therefore, through the PCA technique the original data load has been reduced, while maintaining all of the data information. The previously tri-variate data can now be presented as bi-variate data, making it easier to identify relationships within the data that were not apparent when displayed as tri-variate data.

While the preceding explanation serves to cover the process of PCA, with a relatively simple set of data, PCA analysis finds its true value when analyzing multivariate data comprising many variables, such as data representative of the ECG morphological features found in an electrocardiogram. When analyzing multivariate data, multiple principal components may be extracted to further reduce the data load while retaining correlated data. For each principal component vector that is extracted, variance is removed from the overall multivariate data set. The extraction of each additional principal component removes a decreasing amount of data variance. In generalized multivariate data, assuming data with more than six variables, the extraction of six principal component vectors typically extracts over 95 percent of the total variance, depending upon the number of variables included in the multivariate set. In the example of a multi-lead ECG T wave, usually the first three principal components may represent more than 98 percent of total variance. Depending upon the application, more or less principal component vectors may be extracted to achieve the desired amount of data reduction. Additional information regarding PCA may be found in *Statistics Methods and Applications* by Pawel Lewinski and Thomas Hill.

As the extracted principal component vectors are representative of the dominant correlation remaining in the multivariate data set, analysis of each of the extracted principal component vectors can identify specific correlations between features or variables within a multivariate set. From this, the correlations may be identified, or confidence intervals for specific features, may be determined.

In the current invention, PCA may be used to derive another T wave morphological score based on PCA. The PCA method may be used here to find the most significant components from a group of T wave morphological parameters. A data matrix TM is formed with each column being the values of a particular T wave morphological parameter from multiple ECGs. After running PCA analysis, the first 3 principal components and vectors may be used to derive another score model as:

$$TM\_score\_PCA = b1*Tm1 + b2*Tm2 + b3*Tm3 + bn*Tmn \quad (2)$$

where $b1$-$bn$ are new model coefficients, and $Tm1$-$Tmn$ are eigenvectors of the PCA. Alternatively, the eigenvectors may be known as principal vectors. A similar regression analysis as was applied to model equation (1) is applied to model equation (2) to derive the coefficients.

Figure 3:
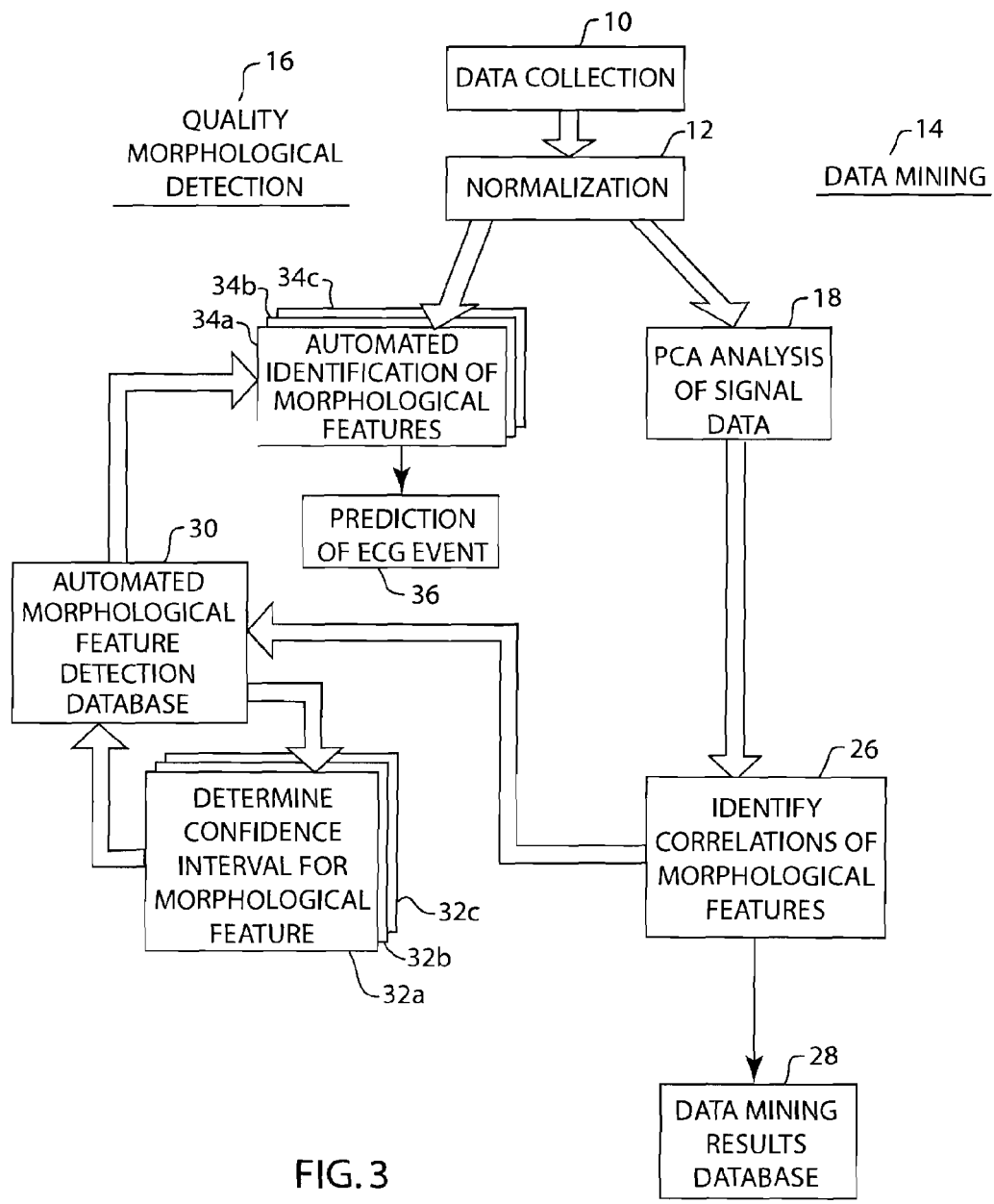
FIG. 3 is a general flow chart showing the steps of an embodiment of the method of the present invention.

FIG. 3 is a general flow chart of the method of the present invention. The method of the present invention begins with the step 10 of collecting patient physiological signal data. While the present description utilizes the collection and analysis of physiological signal data comprising an ECG signal, for exemplary purposes, it is understood that the present invention may be used with other physiological signals, such as EMG or EEG signals, for data mining and/or the measurement quality detection of morphological features. The same is true with respect to the specific exemplary description of the correlation between Q-T interval and TdP, as many physiological signal morphologies may be used in accordance with the present invention.

Once the signal data is collected at step 10, the data is then normalized at step 12. The normalization of the signal data facilitates the comparison of signals utilized in the method of the present invention.

The present invention encompasses two distinct aspects to which steps of the method of the present invention may be directed. These steps may be used individually or in combination to achieve one or both of the goals of data mining using the steps under 14 along the right-hand side of FIG. 3 and ascertaining the quality of detection of morphological features using the steps under 16 along the left-hand side of FIG. 3.

First, the steps shown under 14 and aimed toward data mining, or the identification of predictive features, will be discussed. The patient physiological data that has been normalized in step 12 undergoes a principal component analysis in step 18. In an embodiment of the present invention, six principal component vectors are extracted from the physiological data, thereby encompassing approximately 95 percent of the signal data into the component vectors. It is understood that in embodiments of the present invention more or fewer principal component vectors may be extracted as may be determined by the complexity of the signal being analyzed and/or the complexity of the morphological features to be analyzed.

After the patient physiological data has undergone principal component analysis in step 18, the results of the PCA analysis are used in step 26 to identify correlations between morphological features of the physiological signal data collected in step 10, such as the length of the Q-T interval and the ventricular tachycardia that characterizes Torsade-de-Pointes. Any identified correlations between morphological signals may then be reported to a clinician or stored in a data mining results database 28.

In an embodiment of the present invention, the data collection of step 10 need not comprise just the collection of a single patient ECG signal, but rather an entire database of ECG signals that have been collected throughout a drug trial. As the entire database is run through the steps just described, the step 26 of identifying correlations of morphological features results in the end product of the data mining process 14 aspect of the method of the present invention.

Figure 4:
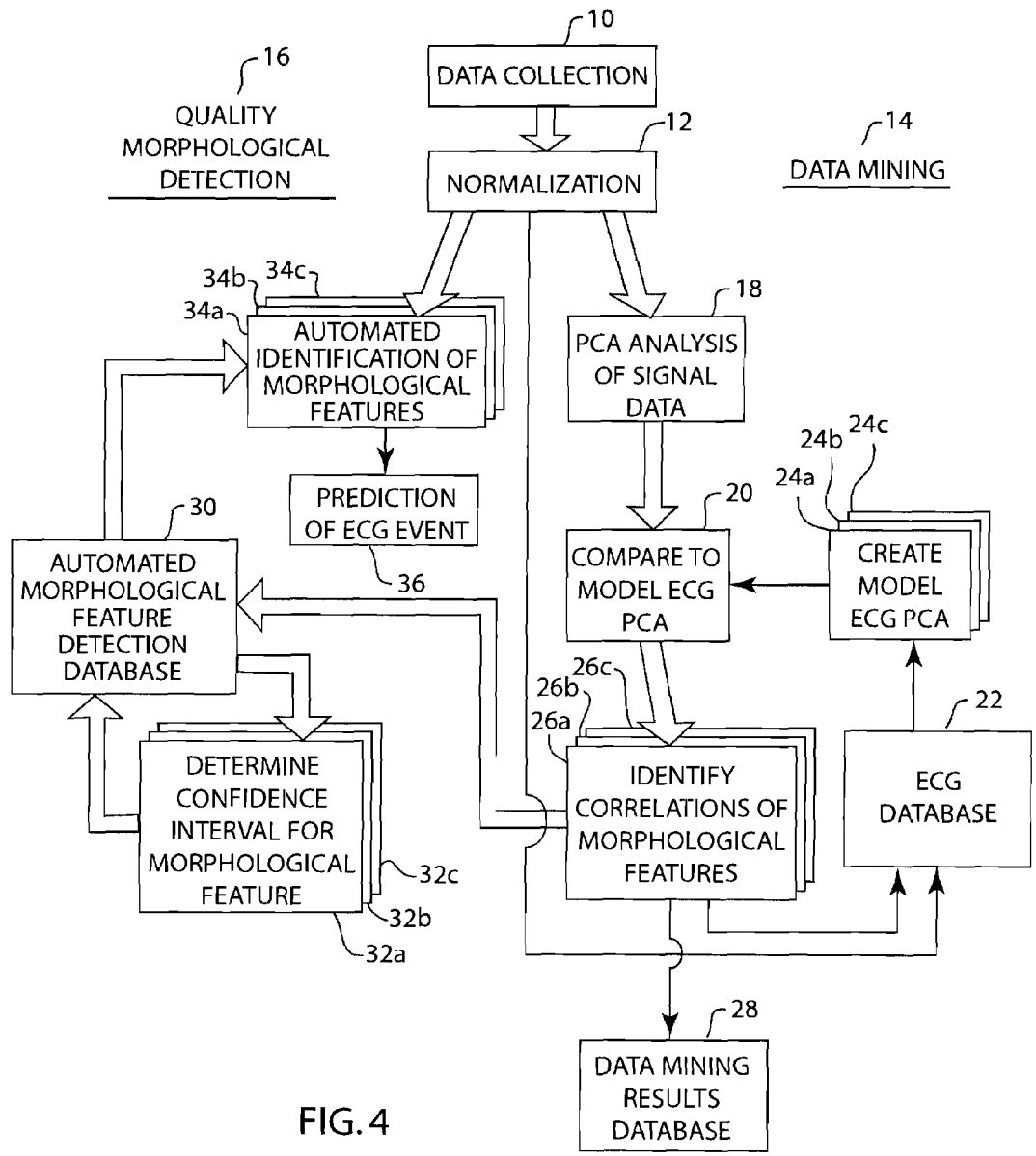
FIG. 4 is a more specific flow chart showing the steps of an embodiment of the method of the present invention.

FIG. 4 is a more detailed flow chart depicting a further embodiment of the method of the present invention relating to data mining. This embodiment employs an ECG signal data database 22. The ECG signal data database 22 comprises ECG signals obtained from many samples. The ECG signal data database 22 may be developed from many sources of ECG signal data that have previously been collected from patients and determined to be of high quality. The data may also be ECG signal data that has been edited so that it is representative of quality ECG signals. The ECG signal data database 22 of the embodiment depicted in FIG. 4 may also include a wide variety of normal and abnormal ECG signal samples, and signals representative of specific ECG morphologies. Therefore, the database provides representative data so that analyses for specific characteristics indicative of specific ECG abnormalities can be performed.

Signals from ECG signal data database 22 are used to create a model ECG principal component analysis in step 24. The creation of the model principal component analysis in step 24 allows a clinician to select specific ECG signal data or groups of ECG signal data from the ECG signal data database 22 in order to create a specifically tailored ECG model principal component analysis to aid in analyzing specific portions, components, or features of the collected patient ECG signal data. As depicted in FIG. 4, multiple model ECG PCA's may be created as in steps 24a, 24b, and 24c, each tailored to being representative of a specific ECG morphology. Such model PCA's may include, for example, an elongated Q-T interval 24a, P wave morphology 24b, or an inflected QRS complex 24c.

Each of these model PCA's are then compared to the PCA carried out at step 18 of the physiological data collected at step 10. The comparison of the model ECG principal component analysis to the collected ECG principal component analysis in step 20 leads to the identification of correlations between specific morphological features present in an ECG signal in step 26. The indications 26a, 26b, and 26c note the use of multiple model ECG PCA's. It is in this embodiment of the method of the present invention that the comparison of the principal component analysis of the collected ECG signals to the PCA of the model ECG signals in step 20 enables the method to identify new features that might comprise an improved indicator of potential adverse health consequences to a patient. For example, regulatory authorities may want to know whether, during the clinical trials of pharmaceutical testing, the drug produces an elongated Q-T interval. Therefore, when using the method of the present invention, ECG signals with an elongated Q-T interval are selected from the ECG signal data database 22. These representative signals are used to create a model PCA of an ECG with an elongated Q-T interval in step 24. The model PCA is compared to the drug trial PCA of step 18 in step 20. The comparison is step 20 will identify the correlation, if any, between an elongated Q-T interval and the drug trial data in step 26 and these results can be reported to the regulatory authorities.

The results of the data mining may be stored in a data mining database 28 of data mining results to further facilitate the identification of morphological features having predictive capability. Alternatively, the results of the correlation identifying step 26 may be added to the ECG signal data database created at 22 to further enhance the number and quality of the ECG signal data within the ECG signal data database 22. In such a manner, the model PCA's created from database 22 would improve over time as the ECG database becomes larger.

Figure 5:
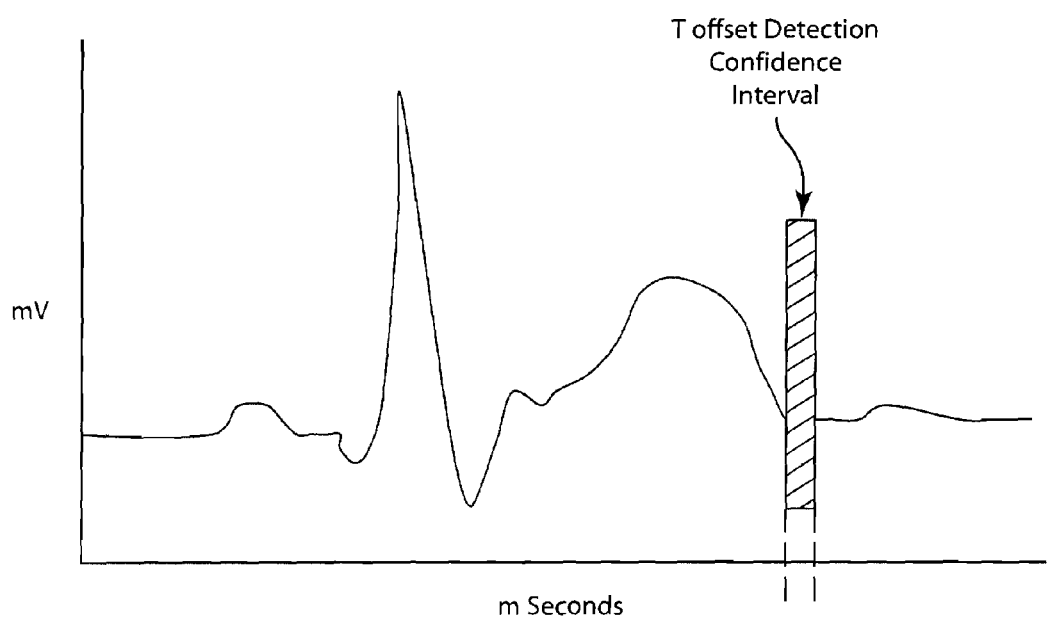
FIG. 5 depicts a confidence interval for the detection of an ECG signal feature.

In an embodiment, the correlations between morphological features of the ECG signal identified in step 26 are then used to determine a confidence interval for specific morphological features at step 30. As depicted in FIG. 5, the confidence interval is the area within which one statistically expects to find a certain morphological feature an identified percentage of the time. FIG. 5 depicts a hypothetical 90 percent confidence interval for the T-wave offset, or the end of the T-wave. This means that in 90 percent of all ECG signals, one can expect to find the end of the T-wave to be within this interval, shown for exemplary purposes as a band of about 20 mseconds.

Once the morphological features of an ECG signal are identified in step 26, the ECG signal is stored and sorted in an automated morphological feature detection database 30. In this database 30 the ECG signal are stored in bins grouping the ECG signals with other ECG signals with similar morphological features. This grouping of the ECG signal into bins of signals with similar morphological features is then utilized in step 32 to improve the determination of confidence intervals for each morphological feature. In step 32 an improved confidence interval for a particular morphological feature may be obtained due to the improved grouping of the ECG signals by their morphological features that were achieved by the identification of the morphological features in step 26. The confidence intervals for a number of different morphological features may be determined at steps 32, 32b, 32c, etc. as shown in the general and specific flow charts of FIGS. 3 and 4, respectively.

In an embodiment, after the ECG signals have been grouped into bins and stored the automated morphological database 30 a statistical analysis may be performed on the ECG signals of each bin, such that the quality of the signals within the bin may be determined. This statistical analysis may utilize an average ECG signal derived from all of the signals stored in the bin, or may use other shaping or feature comparison techniques to determine the quality of the stored signals. Alternatively, ECG signals within a bin with outlying features may be removed from the bin, moved to an alternative bin based upon further analysis of the ECG signal, identifying an alternative morphological feature, or removing the signal from the database 30 all together. In a still further embodiment, as the groups of ECG signals within each bin in the database 30 are analyzed, the system performing the analysis, may learn, and/or optimize the features identified in an ECG signal that cause the signal to be grouped into a particular bin based upon a morphological feature.

The improved determination of confidence intervals for morphological features in step 30 is the first step in achieving the aim of quality morphological feature detection in the steps under the reference numeral 16, represented on the left side of FIG. 4. After the confidence intervals for the morphological features have been determined at step 32, these confidence intervals may be added back into the automated morphological feature detection database 30 shown in FIGS. 3 and 4. The addition of the improved confidence intervals to the stored ECG signals grouped by morphological features, enables the modification of the morphological identification algorithms used in step 34a, 34b, 34c. The modification of the morphological features improves the quality of the automated detection of morphological features in step 34 by increasing the precision with which the algorithms may identify the morphological features.

The process of automated feature detection in step 34 utilizes the data stored in the automated morphological feature detection database 32 to mathematically identify morphological features in the ECG signal data that is being processed. The morphological identification algorithms used in step 34, may comprise average or model ECG signals with a specific morphological feature to which the ECG signal data that is being processed is compared. Similarities between the ECG signal data being processed and the model ECG signal identify the morphological features of the ECG signal data being processed. In an alternative embodiment of the present invention, the PCA analysis between the ECG signal data 18 being processed and the model morphological feature ECG PCA 24 may be used to identify a correlation between the ECG signal data being processed and a morphological feature of the model ECG. A high degree of correlation between the ECG signal data being processed and the model ECG with respect to the morphological feature thus identifies the existence of that morphological feature in the ECG signal data that is being processed.

The method of the present invention therefore commences in taking the patient ECG signal data from a patient in a clinical drug trial at step 10 and normalizing the signal data in step 12 and culminates with the identification of the morphological features of the ECG signal data with increased precision in step 34. The step of identification of morphological features 34 may identify a morphological feature that is indicative of a future adverse ECG event allowing the adverse ECG event to be predicted at step 36. In an embodiment of the present invention, the morphological feature used in steps 30, 32, and 34 is an elongated Q-T interval and the adverse event predicted at step 36 is drug induced TdP.

The method of the present invention provides the advantage over the prior art in that the method of the present invention provides improved data results in two critical areas of pharmaceutical drug testing. The method of the present invention provides the advantage of improved data mining capability for the detection of correlated ECG morphological features by analyzing the data in such a way as to reduce the significant data load thus enabling the processing of the collected ECG data to look for correlations among many morphological features with greater efficiency. Further, the method of the present invention provides quality morphological feature detection by determining higher quality confidence intervals for the morphological features that have been identified for detection. The increased confidence intervals aid in the automated detection of these ECG morphological predictive features. It is further understood that in an embodiment of the present invention, the automated detection of morphological features within the ECG signal may then be used to mark these morphological features in ECG signal data presented to a technician or clinician for review as an aid to the reviewer's own analysis of the ECG signal data.

Figure 6:
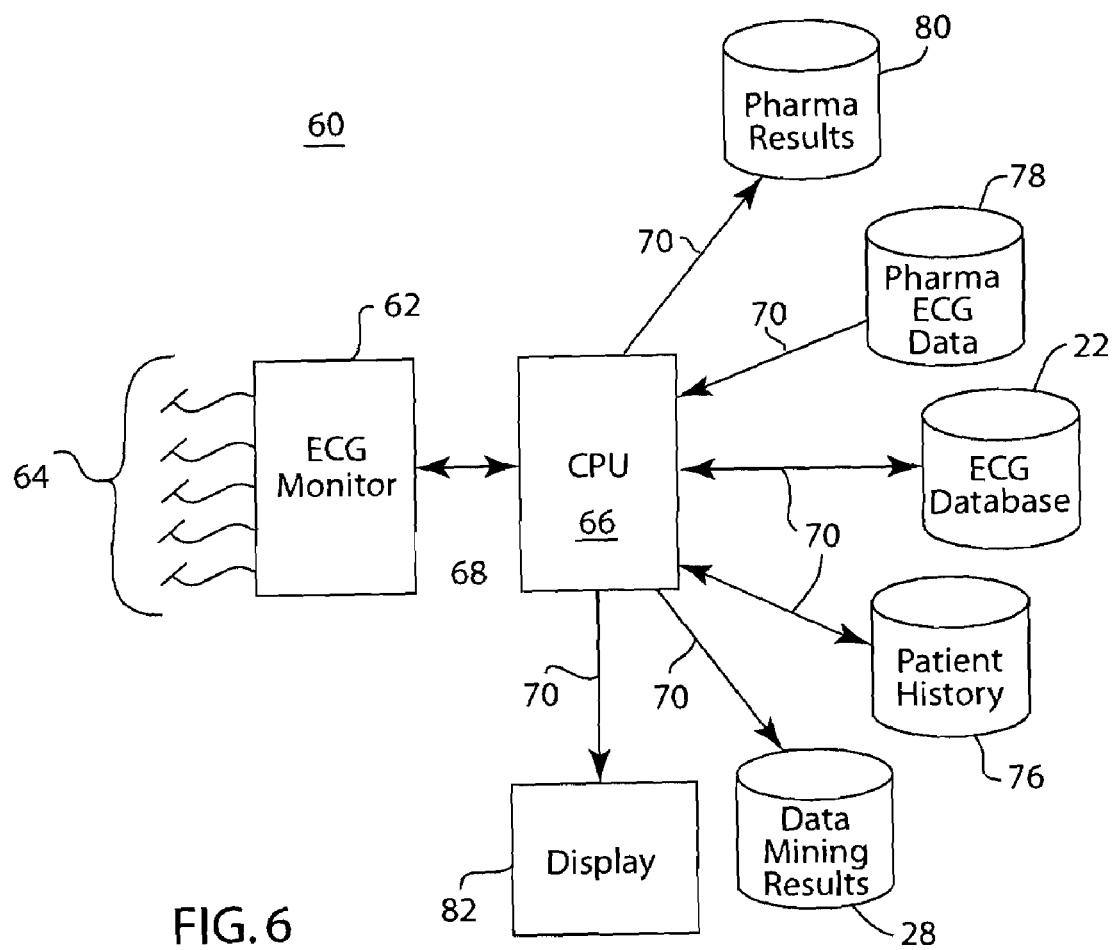
FIG. 6 shows apparatus suitable for carrying out the method of the present invention.

FIG. 6 depicts an embodiment of an apparatus 60 suitable for carrying out the method of the present invention. The apparatus 60 comprises an ECG monitor 62 connected to a plurality of electrodes 64 which are connected to a patient to obtain electrocardiographic signal data from the patient. The ECG monitor 62 is in electrical communication with a CPU 66 via a communication connection 68. It is understood that within the present invention, the CPU 66 may also comprise any other type of processor and/or controller that may be suitable for performing mathematical or logical operations in accordance with the present invention. The CPU 66 is connected via a plurality of communication connections 70 to a variety of databases such as an ECG database 22, a data mining results database 28, a patient history database 76, a pharma ECG data database 78, and a pharma result database 80. Furthermore, the CPU 66 may be connected to a display 82 via a communication connection 70.

In a brief overview of the operation of the apparatus 60 in carrying out an embodiment of the method of the present invention, ECG signals are collected from a patient (not depicted) via the electrodes 64 and received by the ECG monitor 62. The ECG monitor 62 forwards standardized ECG leads from the ECG signals and transmits the ECG leads to the CPU 66 via the communication connection 68. The CPU 66 processes the ECG leads in accordance with the method of the present invention, receiving data from the ECG database 22, or the patient history database 76 as needed. In a data mining capacity, the CPU 66 may transmit data mining results via communication connection 70 to the data mining results database 28. Alternatively, the CPU 66 may transmit data indicative of the identification of morphological features in the patient's ECG signal to a display 82, or the identification of the morphological features may be transmitted to a patient history database 76. In a pharmacological study application of the method of the present invention, the CPU 66 may receive an entire set of pharma ECG data compiled over a series of ECG pharmacological tests from the pharma ECG database 78. The CPU 66 may process the pharma ECG data in accordance with the method of the present invention and transmit any data indicating the detection of TdP or other morphological features to a pharma results database 80.

It is further understood that within the scope of the present invention, the communication connection 68 and the communication connections 70 need not be limited to wired connection, but may comprise wireless technology or may comprise communication connections via the internet or an intranet of a hospital or research facility. It is further understood that within the apparatus for carrying out an embodiment of the method of the present invention all of the databases herein described may be physically located on the same storage device and this storage device may be a data server utilized by a hospital or research facility.

In a further embodiment of the apparatus for carrying out an embodiment of the method of the present invention, the ECG monitor 62 may be integrated into the CPU 66 such that the CPU 66 performs all of the functionality of a standalone ECG monitor 62 and also provides the prescribed functionalities of the CPU 66. In a further embodiment, the functionalities of the CPU 66 may be performed by the ECG monitor 62, as an ECG monitor 62 would typically comprise its own processor or controller that may have the ability to perform the functionalities of the CPU 66.

This written description uses examples to disclose the invention, including the best mode, and also to enable any person skilled in the art to make and use the invention. The patentable scope of the invention is defined by the claims and may include other embodiments within the scope of the invention that occur to those skilled in the art.

Various alternatives and embodiments are contemplated as being with in the scope of the following claims, particularly pointing out and distinctly claiming the subject matter regarded as the invention.

What is claimed is:

1. A computer-implemented method of analyzing patient physiological data collected as part of a pharmacological study, comprising a non-transitory computer-readable medium programmed with computer readable code, such that when a computer processor executes the computer readable code, the processor performs the steps of:
   receiving patient physiological data;
   normalizing the patient physiological data;
   performing a principal component analysis of the normalized patient physiological data;
   comparing the principal component analysis of the normalized patient physiological data to a model patient physiological data principal component analysis, wherein the model physiological data principal component analysis is representative of a specific physiological morphological feature;
   using the comparison to identify if the specific physiological morphological feature is present in the patient physiological data.

2. The method of claim 1 wherein the patient physiological data is patient ECG signal data.

3. The method of claim 2 wherein the model patient physiological data principal component analysis is created by a principal component analysis of a plurality of ECG signal data exhibiting the specific morphological feature.

4. The method of claim 3 wherein a model physiological data principal component analysis is created using a plurality of edited normal and abnormal ECG signals.

5. The method of claim 3 wherein the specific physiological morphological a T-wave characteristic.

6. The method of claim 3 wherein the specific physiological morphological feature comprises at least one of a first upslope line, a second upslope line, a T peak line, and a down slope line.

7. The method of claim 2 further comprising the step of sorting the patient ECG signal data into morphological bins based upon the presence of the specific morphological feature identified in the comparison of the patient ECG signal principal component analysis to the model physiological data principal component analysis.

8. The method of claim 7 further comprising the step of performing a statistical analysis on the ECG signals in each morphological feature bin to determine the quality of an individual signal within the bin.

9. The method of claim 7 further comprising the step of determining a confidence interval for each morphological feature bin, the confidence interval reflecting the amount of variance in the specific morphological feature in the patient ECG signal data.

10. The method of claim 9 further comprising the step of rejecting patient ECG signal data based upon its deviation from the other patient ECG signal data within the same bin.

11. The method of claim 7 further comprising the step of learning identifying characteristics of each bin and using the learned identifying characteristics to automatically detect and identify desired predetermined selected signal morphology in the analysis of an ECG signal.

12. The method of claim 9 further comprising creating a morphological identification algorithm for a plurality of the patient ECG signal data in a morphological bin.

13. The method of claim 12 wherein the morphological identification algorithm is an average of the patient ECG signal data in the morphological bin.

14. The method of claim 13 further comprising applying the morphological identification algorithm to newly collected patient ECG signal data to determine if the specific morphological feature is present in the newly collected patient ECG signal data.

15. A method of analyzing an ECG signal collected as part of a pharmacological drug trial, the method comprising the steps of:
    collecting ECG signal data;
    performing principal component analysis on the collected data;
    identifying characteristics of the ECG signal data by comparing the principal component analysis of the ECG signal data to a plurality of model principal component analysis, each of a specific morphological feature;
    sorting the ECG signal data into groups based upon the identified characteristics;
    performing a statistical analysis on the ECG signal data groups to determine an indication of ECG signal data group quality;
    using the ECG signal data group and the indication of ECG signal data group quality to derive a morphological detection algorithm.

16. The method of claim 15 wherein the step of collecting ECG signal data comprises receiving the ECG signal data from a database of collected ECG signal data.

17. The method of claim 15 wherein the indication of signal quality is a confidence interval for detecting a specific morphological feature in collected ECG signal data.

18. The method of claim 17 further comprising:
    receiving new ECG signal data;
    applying the morphological detection algorithm to the ECG signal data to determine if the specific morphological feature is present in the new ECG signal data.

19. The method of claim 18 wherein the specific morphological feature is Torsade-de-Pointes.

20. A computer program embodied on a non-transitory computer-readable medium having computer logic for enabling at least one processor in a computer system to facilitate analyzing an ECG signal collected as part of a pharmacological drug trial, the non-transitory computer-readable medium comprising:
    a first computer readable program code portion for collecting ECG signal data;
    a second computer readable program code portion that perform a principal component analysis (PCA) of the collected ECG signal data to obtain a collected ECG signal data PCA, comparing the collected ECG signal data PCA to a plurality of model morphological feature PCA, and sorts the collected ECG signal data into groups based upon to which of the plurality of model morphological feature PCA the collected ECG signal data PCA is the most similar;
    a third computer readable program code portion creating a model of the ECG signal data in each of the groups; and
    a fourth computer readable program code portion using the model to detect a morphological feature of a future ECG signal.

* * * * *